United States Patent [19]

Gambale et al.

[11] Patent Number: 5,060,660
[45] Date of Patent: Oct. 29, 1991

[54] STEERABLE EXTENDABLE GUIDEWIRE WITH ADJUSTABLE TIP

[75] Inventors: Richard A. Gambale, Tyngsboro; James S. Hunter, Westford, both of Mass.

[73] Assignee: C. R. Bard, Inc., Murray Hill, N.J.

[21] Appl. No.: 486,515

[22] Filed: Feb. 28, 1990

[51] Int. Cl.⁵ .............................................. A61B 5/00
[52] U.S. Cl. .................................... 128/772; 604/170
[58] Field of Search .............................. 128/656–658, 128/772; 604/95, 170, 280, 282

[56] References Cited

U.S. PATENT DOCUMENTS

| 4,456,017 | 6/1984 | Miles | 128/772 |
|---|---|---|---|
| 4,543,090 | 9/1985 | McCoy | 604/95 |
| 4,545,390 | 10/1985 | Leary | 128/772 |
| 4,573,470 | 3/1986 | Samson et al. | 128/344 |
| 4,582,181 | 4/1986 | Samson | 128/348.1 |
| 4,650,467 | 3/1987 | Bonello et al. | 604/95 |
| 4,719,924 | 1/1988 | Crittenden et al. | 128/772 |
| 4,721,117 | 1/1988 | Mar et al. | 604/170 |
| 4,732,163 | 3/1988 | Bonello et al. | 128/772 |
| 4,734,093 | 3/1988 | Bonello et al. | 604/95 |
| 4,798,598 | 1/1989 | Bonello et al. | 604/280 |
| 4,799,496 | 1/1989 | Hargreaves et al. | 128/772 |
| 4,815,478 | 3/1989 | Buchbinder et al. | 128/772 |
| 4,827,941 | 5/1989 | Taylor et al. | 128/772 |
| 4,884,579 | 12/1989 | Engelson | 604/170 |
| 4,886,067 | 12/1989 | Palermo | 128/772 |
| 4,921,482 | 5/1990 | Hammerslag et al. | 128/772 |
| 4,928,669 | 5/1990 | Sullivan | 128/772 |
| 4,940,062 | 7/1990 | Hampton et al. | 128/772 |

Primary Examiner—Max Hindenburg
Attorney, Agent, or Firm—Wolf, Greenfield & Sacks

[57] ABSTRACT

A small diameter steerable guidewire for cardiovascular catheterization procedures is provided with a means by which the curvature at the distal tip of the guidewire can be adjustable by control applied at the proximal end of the guidewire whereby the curve at the distal end of the guidewire can be adjusted without requiring removal of the guidewire from the patient. The proximal end of the guidewire is configured so that it can be attached to a guidewire extension so as to facilitate catheter exchanges.

19 Claims, 4 Drawing Sheets

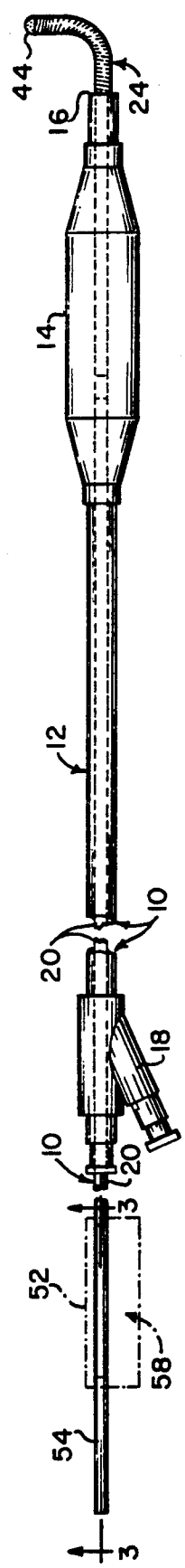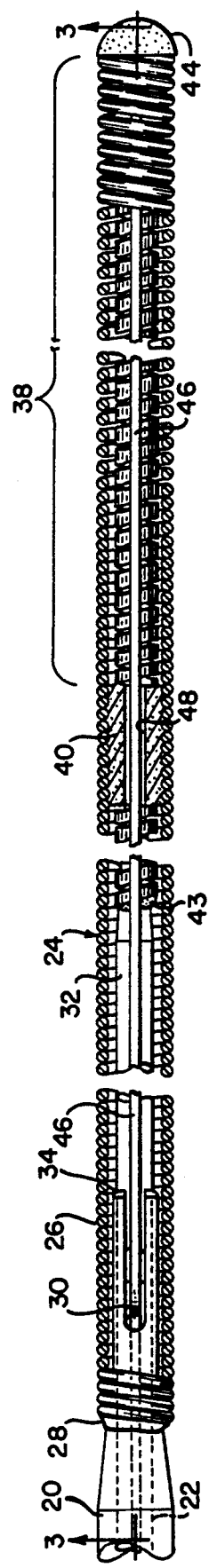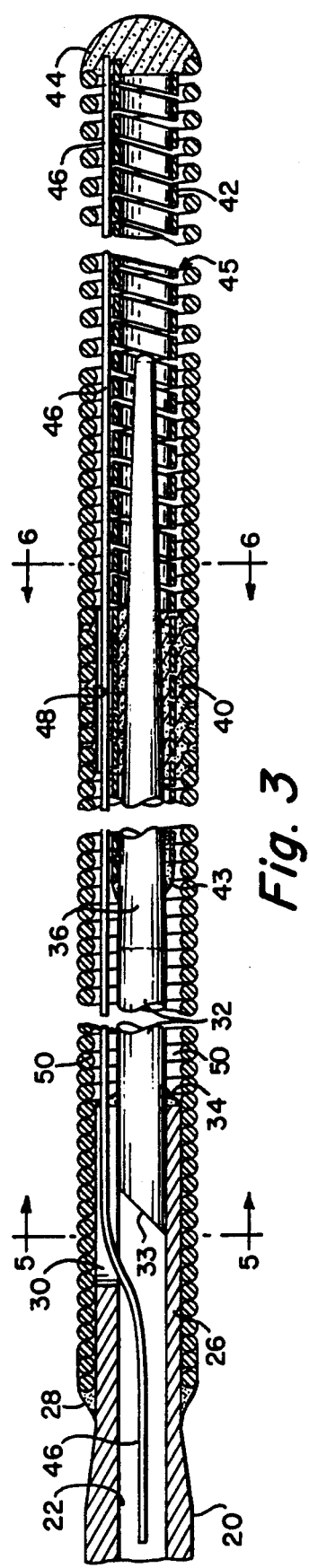

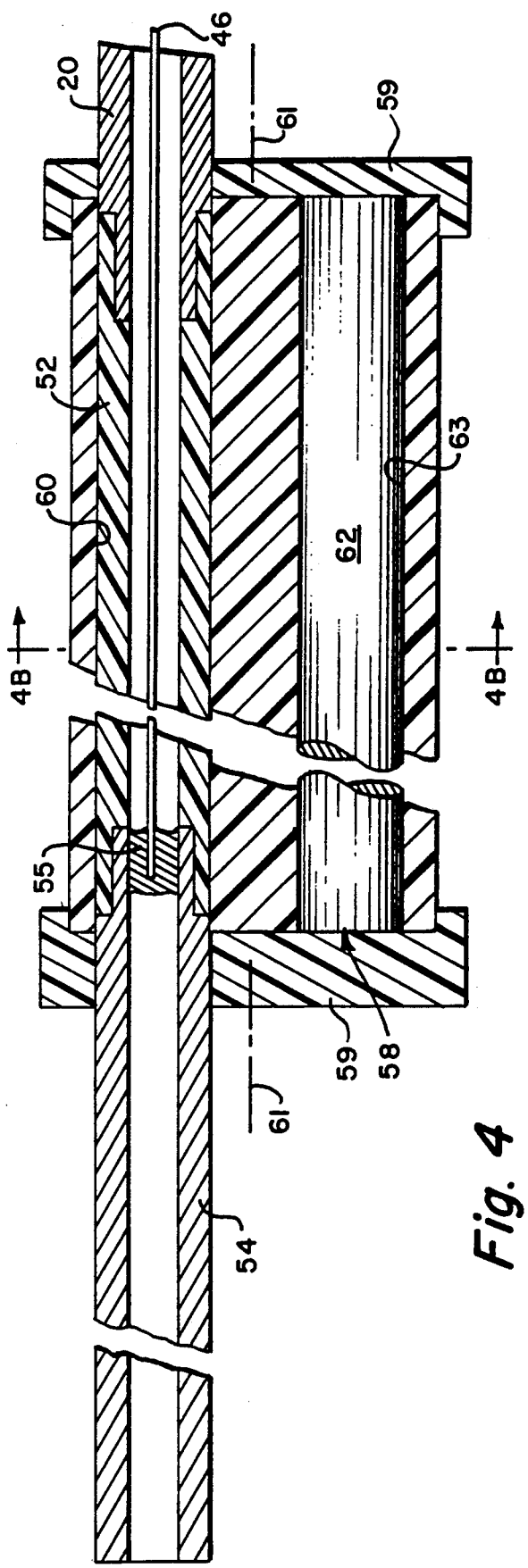
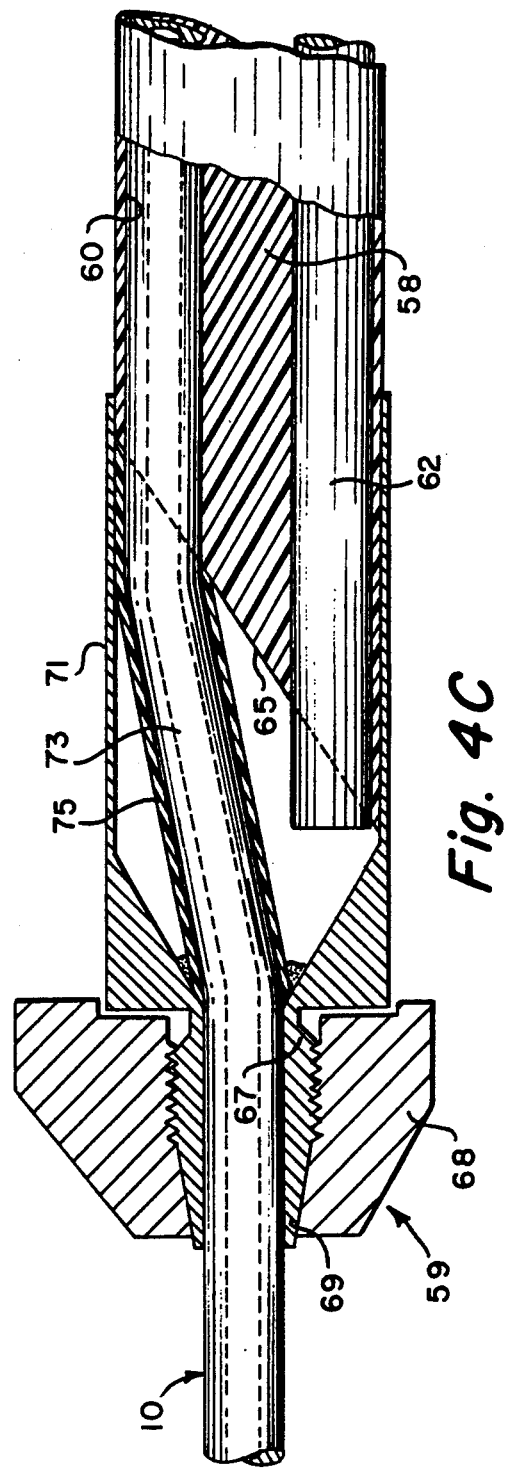
Fig. 4
Fig. 4C

STEERABLE EXTENDABLE GUIDEWIRE WITH ADJUSTABLE TIP

FIELD OF THE INVENTION

This invention relates to guidewires used in the placement of catheters in a patient's cardiovascular system and, particularly, to improvements in small diameter steerable guidewires to facilitate such placement.

BACKGROUND OF THE INVENTION

This invention relates to improvements in guidewires, particularly guidewires used in small bore blood vessels such as those involved in angioplasty procedures. U.S. Pat. No. 4,545,390 to Leary discloses a small diameter (no greater than about 0.020" in diameter) steerable guidewire which can be advanced and steered into and along very narrow blood vessels to locate the distal end of the guidewire in a precise position in a selected blood vessel branch. Once the guidewire has been so placed, a catheter can be advanced over the guidewire directly to the desired location in the patient's cardiovascular system to enable the catheter to perform its intended function at that location. For example, such guidewires are particularly useful in coronary angioplasty procedures in which a small diameter balloon dilatation catheter is placed in a narrowed region of a coronary artery so that the balloon may be inflated to widen the lumen of the artery and improve blood flow through the artery.

U.S. Pat. No. 4,545,390 to Leary discloses a small diameter steerable guidewire which is capable of transmitting from its proximal end to its distal end substantially all of the angular rotation applied to the proximal end. The distal end of the guidewire is adapted to be bent to a set curve by the surgeon before the guidewire is placed in the patient. After the guidewire has been placed in the patient's blood vessel, it may be steered to select between branches of the patient's cardiovascular system by rotating the proximal end of the guidewire to direct selectively the bent distal end of the guidewire to the desired branch. Typically, the guidewire is advanced through the blood vessels while being monitored fluoroscopically.

The curve which the physician forms at the distal tip of the guidewire, before inserting it into the patient, necessarily involves an approximation as to the degree of curvature best suited for the particular procedure to be performed. Sometimes, after the guidewire has been placed, the degree of bend placed in the distal tip proves to be too great or too little to enable the tip to be steered into a selected blood vessel. Under those circumstances, the physician may have to withdraw the guidewire, reform the bend at its distal tip and then reinsert the guidewire. That complicates and delays the procedure undesirably. In order to overcome that limitation, a small diameter steerable guidewire was developed in which the degree of curvature at the distal tip of the guidewire could be adjusted and controlled while the guidewire remained in place in the patient and without requiring removal and manual reshaping of the guidewire. Such a guidewire is disclosed in U.S. Pat. No. 4,719,924 to Crittenden et al. and includes an elongate torsionally rigid shaft formed from a solid walled tube. The distal end of the guidewire includes a core wire that is attached to and extends from the distal end of the solid walled tube and the helical coil arrangement that extends about the core wire. A pull wire extends through the full length of the guidewire and is connected at its distal end to the distal end of the spring. The proximal end of the pull wire extends through the spring arrangement and into the solid walled tube and exits at the proximal end of the shaft. An arrangement is provided at the proximal end of the guidewire to vary the tension on the pull wire to cause the distal end of the guidewire to assume a degree of curvature depending on the extent of pull applied to the pull wire.

Also among the desirable features in guidewires is the ability to extend the length of the guidewire, from its proximal end, in order to facilitate catheter exchanges over the guidewire. As described in U.S. Pat. Application Ser. No. 206,008, filed June 13, 1988, the proximal end of the guidewire that extends out of the patient is relatively short. In order to exchange the indwelling catheter for a different catheter, for example, to use a different size balloon, an extension wire may be attached to the proximal end of the guidewire that extends out of the patient. The extension wire is of a length such that its total length, together with the exposed length of the proximal end of the indwelling guidewire is greater than the length of each of the indwelling and replacement catheters. Thus, when the catheter is withdrawn, some portion of the guidewire will be exposed and grippable by the physician or an assistant in order to assure that the position of the guidewire in the patient will be maintained during the catheter exchange procedure. As described in Application Ser. No. 206,008, the proximal end of the guidewire and the distal end of the extension wire are provided with connector means by which they may be detachably connected. The connector means is such that it does not present an enlarged cross sectional configuration greater than that of the guidewire itself in order that the catheters may be advanced smoothly over the connected wires. To that end, the connector element on the proximal end of the guidewire is in the form of a slender tubular member defining a socket which is receptive to a small diameter latching arrangement carried by the distal end of the extension wire, the latching arrangement being insertable in and mechanically interlockable with the tubular socket.

Although it would be desirable to provide a guidewire having the ability to adjustably control the curvature at the distal tip of a guidewire while also providing a capability for attaching an extension wire to permit catheter exchanges to be performed, those objectives have not been achievable previously in the same guidewire because the control device for operating the pull wire necessary for the adjustable J feature would not permit connection of a guidewire extension or provide a low profile over which catheters could be advanced in order to perform a catheter exchange. It is among the objects of the invention to provide such a guidewire having both capabilities.

SUMMARY OF THE INVENTION

In accordance with the invention, the shaft and distal portion of the guidewire may incorporate the configuration and structure described in U.S. Pat. No. 4,719,924. Attached to the proximal end of the torsionally rigid solid walled tubular shaft is a flexible somewhat elastic tubular segment through which the pull wire extends. Attached to the proximal end of the flexible elastic tubular segment is an elongate tubular socket which serves as the socket portion of the connector means for connection with an extension wire. The proximal end of the pull wire is attached securely to the region of the juncture of the flexible tube and connector socket. The flexible tube is configured so that it may be stretched by the physician, thereby applying a tension to the pull wire which is transmitted to the distal end of the guidewire, thus causing the distal tip of the guidewire to assume a curved shape. In the preferred embodiment of the invention, the flexible tube is caused to stretch by bending it. Preferably the flexible tube is bent in a manner such that the degree of curvature at the distal tip of the guidewire is a direct function of the degree of curvature applied to the flexible tube at the proximal end of the guidewire. Because the flexible tubular portion, the guidewire shaft and the tubular connector socket are of the same outer diameter, the profile of the guidewire is maintained uniform and low sufficiently so that catheters may be advanced over it when the guidewire is connected to the extension wire.

In another facet of the invention, a means is provided to facilitate bending the flexible tube into a stretched condition and for securely retaining the flexible portion of the shaft in a selected bent configuration so that the physician does not have to manually maintain the stretch of the flexible tube. To that end, a curve retention device is provided. The curve retention device includes an outer sleeve having two bores, one to receive the guidewire and another that contains an internal malleable wire. The guidewire receiving bore is displaced laterally of the central axis of the sleeve. In use, the sleeve is placed over the flexible tubular segment and is clamped to the ends of the sleeve by clamps at the ends of the sleeves. The two then are bent together with the guidewire containing bore disposed on the radially outward side of the bend. Bending the assembly in that manner stretches the proximal end of the guidewire causing the flexible tubular portion to stretch thereby to cause the pull wire to apply a tension to the distal end of the guidewire. The malleable element in the wall of the sleeve maintains the flexible tubular segment in any desired curved configuration set by the physician. The degree of curvature at the distal end of the guidewire may be determined simply by observing the degree of curvature at the flexible tubular segment. Should it be desired to perform a catheter exchange, the guidewire is made ready for the exchange by slipping the sleeve off the proximal end of the guidewire and attaching a guidewire extension to the socket at the proximal end of the guidewire.

It is among the general objects of the invention to provide a guidewire which has capability both to controllably adjust the degree of curvature at the distal end of the guidewire by manipulation from the proximal end of the guidewire while also permitting a guidewire extension to be attached to the guidewire and enabling a catheter exchange to be performed.

Another object of the invention is to provide a guidewire having an adjustably curvable tip which may be controlled from the proximal end of the guidewire and in which the means for controlling the degree of pull does not permanently add to the profile of the guidewire.

Another object of the invention is to provide a guidewire having an adjustable J tip in which the curvature at the distal tip can be controlled by one hand at the proximal end of the guidewire.

A further object of the invention is to provide a guidewire of the type described and a detachably connectable means for retaining the curvature at the distal tip of the guidewire in a selected curved configuration.

DESCRIPTION OF THE DRAWINGS

The foregoing and other objects and advantages of the invention will be appreciated more fully from the following further description thereof, with reference to the accompanying drawings wherein:

FIG. 1 is a fragmented side elevation of a catheter with the guidewire of the invention extending through the catheter;

FIG. 2 is an enlarged, fragmented and broken away illustration of the distal region of the guidewire;

FIG. 3 is a further enlarged sectional illustration of the guidewire as seen along the line 3—3 of FIG. 2;

FIG. 4 is a sectional illustration of the tip adjustment portion of the proximal end of the guidewire as seen along the line 4—4 of FIG. 1 with the retaining sleeve in position on the guidewire;

FIG. 4C is a less diagrammatic illustration of one end of the retaining sleeve illustrating, in further detail, the preferred embodiment of the clamping arrangement for detachably securing the sleeve to the guidewire;

DESCRIPTION OF THE PREFERRED EMBODIMENT

Figure 4A:
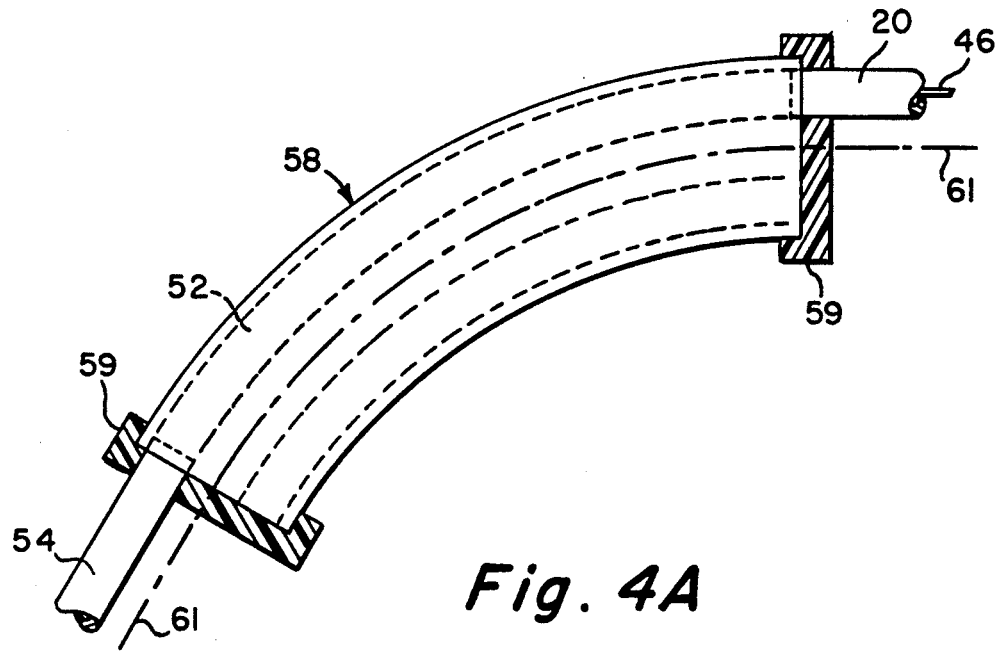
FIG. 4A is an enlarged diagrammatic illustration of the proximal end of the guidewire with the retaining sleeve disposed over the proximal end of the guidewire and with the retaining sleeve and flexible segment being bent to apply tension to the pull wire.

FIG. 1 illustrates the guidewire 10 of the present invention in combination with a balloon dilatation catheter 12. The catheter 12 may be generally of the type described in U.S. Pat. No. 4,545,390 to Leary. The dilatation catheter 12, particular when intended for use in a small artery such as a coronary artery, is relatively slender and, for example, may have an outer diameter of the order of 0.050". The inner dimensions of its lumens, of course, are even smaller and its main lumen may be of the order of 0.022" diameter at its smallest cross sectional dimension. The catheter has a dilatation balloon 14 at its distal end and a central lumen which receives a guidewire and which is used to deliver liquids such as radiopaque dyes or anticoagulants and also to make distal pressure measurements. The guidewire lumen of the catheter 12 opens at an outlet 16 at the distal tip of the catheter. The catheter also is provided with an inflation lumen (not shown) which is smaller and communicates with the interior of the balloon 14 to inflate and deflate the balloon. The proximal end of the catheter may be provided with a Y-fitting 18 to provide communication at the proximal end of the catheter to each of the central and inflation lumens of the balloon dilatation catheter 12.

As shown in FIGS. 1-3, the guidewire of the present invention includes an elongate shaft 20 which is hollow and is in the form of a solid walled tube having a central lumen 22. The shaft 20 may be formed from stainless steel hypodermic tubing. The shaft 20 extends along the major portion of the length of the guidewire. By way of example, in a guidewire having an overall length of about 180 cm, the shaft 20 may have a length of about 155 cm. The shaft has an outer diameter not greater than about 0.016" and, in the illustrative embodiment of the invention, has a wall thickness of 0.003". The solid walled configuration of the shaft is sufficiently torsionally rigid to transmit substantially fully to the distal end of the wire rotation applied at the proximal end. Thus, the distal end of the guidewire 10 can be caused to rotate in controlled increments to permit steering of the guidewire.

An elongate helical outer spring, indicated generally at 24 is attached to the distal end of the shaft 20. The spring 24 extends along a relatively short portion of the overall length of the guidewire 10. For example, a guidewire having an overall length of about 180 cm may have a spring 24 about 25 cm in length. In the preferred embodiment of the invention, the outer diameter of the spring 24 is not substantially greater than that of the shaft 20 and, preferably, is the same diameter as the shaft 20. The distal end of the shaft 20 is reduced in outer diameter as by drawing the wire lengthwise so that it may fit within the proximal end of the spring 24 in a manner which enables the diameter of the spring 24 to remain substantially the same diameter as the shaft 20.

The proximal end of the spring 24 is connected to the tapered end of the shaft 20 by a brazed joint 28. The tapered distal end 26 of the shaft 20 is provided with a longitudinal slot 30 to permit passage of a pull wire, as will be described. The guide wire 10 also includes a relatively short distal core wire 32 which is secured to and extends distally from the distal end of the shaft 20. In the illustrative embodiment the core wire is not longer than about 20 cm and may have a diameter of about 0.008". The proximal end of the core wire 32 is received in the opening at the distal end 26 of the shaft 20 and is secured thereto with a brazed joint 34. The proximal end of the distal core wire 32 preferably is beveled, to define an upwardly and distally inclined ramp as indicated in FIG. 3 at 33, and is connected so that it terminates short of the blind end of the slot 30 to maintain a portion of the slot 30 open. The bevel at the end 33 of the core wire 32 enables a substantial portion of the slot 30 to be maintained open while providing an increased area of support for the core wire 32 by the distal end 26 of the shaft 20.

The distal end of the distal core wire 32 is tapered along its most distal four to seven centimeters, as suggested at 36. The tapered configuration provides a progressively increasing flexibility along that portion of the guidewire. The tip of the distal core wire 32 terminates short of the distal tip of the spring 24 so that a distal segment 38 of the spring extends beyond the end of the core wire 32. The distal end of the core wire 32 is secured to the spring 24 at a distal brazed joint 40.

The guidewire includes an inner helical spring 42 which is attached at one end to the tapered portion 36 of the core wire 32 and at its distal end to a hemispherical end cap 44 which also is secured to the end of the outer spring 24. The proximal end of the inner spring 42 may be attached to the distal end of the core wire 32 by incorporating it into the distal brazed joint 40. It also may be connected at a brazed joint 43. The inner spring 42 provides an additional margin of protection against breaking and separation of the distal segment 38 of the guidewire from the spring 24 and thus serves as a safety member. The inner or safety spring 42 preferably is wound from rectangular cross section wire in a helix of opposite direction from that of the outer spring 24. By forming the inner safety spring 42 from a rectangular wire, the outer diameter of the coil may be reduced thus defining in ample somewhat annular space 45 between the outer diameter of the safety spring 42 and the inner diameter of the outer spring 24. As will be described, the annular space 45 (which may be somewhat eccentric as suggested in FIG. 6) receives and provides a channel for a pull wire. The inner safety spring, which is wound in a helix of opposite direction from that of the outer spring 24 provides for additional torsional rigidity at the distal segment 38 of the guidewire but without significantly increasing the flexibility of the segment 38. Winding of the springs 24, 42 in opposite directions also reduces any tendency of the coils of the spring to interlock during operation of the device. As illustrated in FIGS. 2 and 3, the coils of each of the outer spring 24 and inner safety spring 42 may be spaced from each other, as desired, to provide for increased flexibility, as desired.

In accordance with the invention, the configuration of the distal segment 38 of the spring 24 may be controlled to vary the extent to which it is bent or curved without requiring removal of the guidewire from the patient. In accordance with the invention, a pull wire 46, preferably is in the form of a flat stainless steel ribbon having a cross-section of the order of 0.002"×0.003" is provided. It extends the full length of and projects from the proximal end of the guidewire. It is attached at its distal end to the end cap 44, extends proximally through the generally annular region 45 between the inner spring 42 and outer spring 24, then through an aperture 48 formed in the distal joint 40 and then along the annular region 50 defined between the distal core wire 32 and the lumen of the spring 24. The pull wire 46 extends further proximally through the opening defined by the slot 30, into the lumen 22 of the shaft and extends through the lumen of the shaft toward at the proximal end of the shaft 20. The distal segment 38 normally tends to maintain a straight configuration but can be drawn to a curve of varying degree by pulling on the guidewire 46 to the degree desired.

The springs 24 and 42 preferably are formed to maximize the internal diameter of the annular lumens 45, 50 to provide adequate clearance for the pull wire 46 to pass and move freely. In the illustrative embodiment of the invention, the spring 24 may be formed from stainless steel wire having a circular cross-section of 0.002" diameter wound to a spring coil 0.016" diameter The inner spring 42 may be formed from stainless steel wire having a rectangular cross section 0.001"×0.003" wound to a coil defining an outer diameter of 0.009" to 0.010". When used with a distal core wire 32 of the order of 0.008" diameter, the remaining diameter clearances of 0.004" and for the annular spaces 45, 50, respectively are adequate for the pull wire which, preferably, also is formed from rectangular wire 0.001"×0.003".

Preferably, at least a portion of the distal segment 38 is expanded somewhat to separate slightly the helical coils one or both of the springs 24, 42. The proportion of separated helical coils in the distal segment 38 affects the radius to which the distal tip can be curved in response to pulling on the pull wire 46. The separated coils define a more flexible configuration in which the coils do not support each other. Thus, the segment of separated coils is more easily bent and will tend to assume a curved or J shape quite easily in response to tension applied to the pull wire 46. When relatively few of the coils are spaced, pulling on the pull wire 46 will cause them to assume a J-shape while the more proximal unspaced coils in the distal segment will tend to remain straight. Thus, with fewer coils spaced a smaller radius curve is formed. If a greater number of coils in the distal segment are spaced from each other, then the wire will tend to assume a larger radius curve when pull wire 46 is pulled. In the illustrative example of the invention, a portion 51 (see FIG. 7) of the outer spring 24 is formed with the coils close. together while the coils in the more distal portion are spaced. As can be seen from FIG. 7, when the wire is pulled, the segment 51 will tend to remain straight, with the curve in the wire being formed in the more distal portion and with a radius slightly smaller than would have been the case had all of the coils, including the segment 51, been spaced.

Alternately, other tip configurations may be employed, such as, for example, the tip configuration disclosed in U.S. Pat. No. 4,886,067, issued Dec. 12, 1989, the disclosure of which is incorporated herein by reference in its entirety.

Figure 4B:
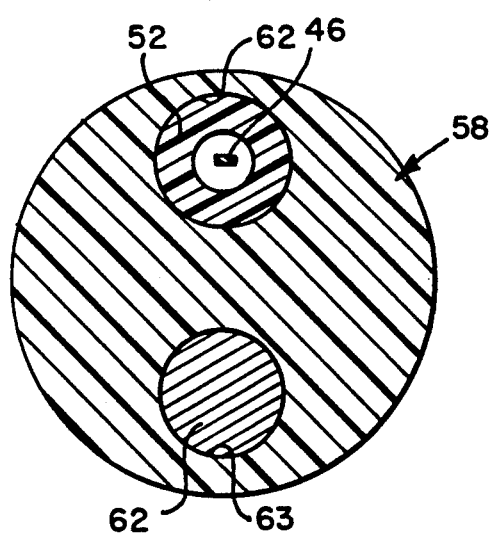
FIG. 4B is a somewhat diagrammatic cross-sectional illustration of the guidewire and retaining sleeve as seen along the line 4B—4B of FIG. 4.
Figures 5, 6, 7, 8:
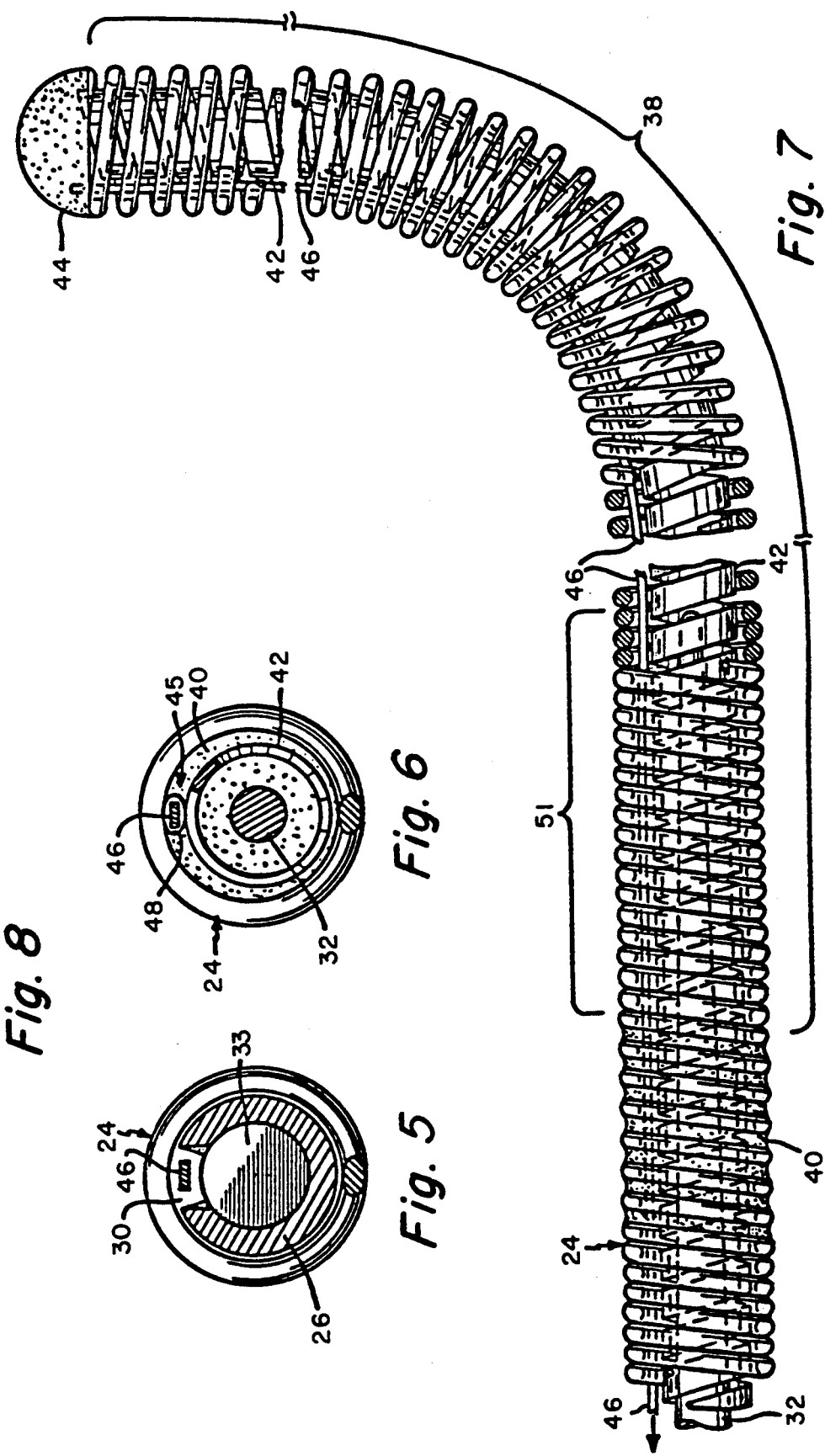
FIG. 5 is a sectional illustration of the guidewire as seen along the line 5—5 of FIG. 3.
FIG. 6 is a sectional illustration of the guidewire as seen along the line 6—6 of FIG. 3.
FIG. 7 is an enlarged illustration of the tip of the guidewire in a curved configuration.
FIG. 8 is a cross sectional fragmented illustration of the proximal end of the guidewire, with the retaining element removed and with the distal end of the extension wire in readiness to be inserted into the tubular socket.

FIG. 4 shows, in enlarged somewhat diagrammatical detail, the configuration of the proximal end of the guidewire and the manner in which the tension is applied to the pull wire 46. The proximal end of the shaft 20 is connected to a short resilient elastic, flexible tubular element 52. The tubular element 52 preferably is formed from a suitable elastomer, such as a thermoplastic rubber available under the trade name Kraton, from the Shell Chemical Company, Chicago, Ill. An appropriate adhesive, such as cyanoacrylate preferably is used to join the elastomeric tube 52 to the metal tube. Attached to the proximal end of the flexible tubular segment 52 is an elongate segment of tubing, such as hypodermic tubing 54 which serves as a socket for the connector end of a guidewire extension, indicated generally at 20 (FIG. 8). The pull wire 46 extends through the flexible segment 52 and is connected, at its proximal end, to the distal end of the socket tubing 54, as by solder indicated at 55. The length of the pull wire and other elements of the guidewire are such that when the flexible elastic segment 52 is unstretched, the distal end of the guidewire will be straight. When tension is applied to the proximal end of the guidewire, the elastic, flexible segment 52 will stretch and the pull wire 46 will be pulled in a proximal direction, to an extent dependent on the degree of stretch of the flexible segment 52. As described, the degree to which the pull wire 46 is pulled controls the degree to which the distal tip of the guidewire is curved.

In order to facilitate stretching of the proximal end of the guidewire and to be able to retain the flexible elastic segment 52 in a stretched condition, a stretching and retention device is provided. As shown diagrammatically in FIG. 4, it includes a detachable sleeve like element, indicated generally by the reference character 58. The sleeve 58 may be formed from an appropriate flexible polymeric material such as a suitably flexible grade of Kraton, available from Shell Chemical Company. The sleeve may be of the order of $\frac{1}{4}''$ to $\frac{1}{2}''$ in diameter and about 3" long. The sleeve 58 is formed to define a bore 60 dimensioned to receive the proximal end of the guidewire. The bore 60 is offset eccentrically, from the longitudinal axis 61 of the sleeve 58. Clamp elements, illustrated diagrammatically at 59 in FIGS. 4 and 4A, and in more details in FIG. 4C, are carried by the sleeve 58 and serve to detachably clamp the ends of the sleeve 58 to the guidewire at locations proximally and distally of the flexible tubular element 52.

When the sleeve 58 is placed over the flexible, elastic tube 52 and is clamped to the guidewire by the clamps 59, the sleeve 58 is bent with the bore 60 and contained tube 52 on the radial outside of the bend (as illustrated in FIG. 4A), the guidewire will stretch in the region of the flexible, elastic tubular segment 52. That applies a tension to the pull wire, causing the tip of the guidewire to bend. A means also is provided to retain the curve at the distal end of the guidewire. To that end, the sleeve 58 also includes an elongate malleable wire element 62 embedded in a second bore 63 in the sleeve. The malleable wire may be formed, for example, from copper and preferably is of a diameter generally corresponding to that of the guidewire itself. The malleable wire 62 will bend in unison with the sleeve 58 and tubular segment 52 to any desired curved configuration and will retain that bent shape when the sleeve 58 is released. Thus, the malleable wire 62 serves to retain the flexible segment 52 in any preset curved configuration thus maintaining the corresponding curvature at the distal end of the guidewire. The physician thus may impart a desired degree of curvature to the distal end with the same hand with which he holds and manipulates the guidewire. Additionally, because the degree of curvature of the distal end of the guidewire is a direct function of the degree of curvature of the flexible segment 52, the physician can determine the degree of curvature at the distal tip by simple reference to the curvature of the flexible segment 52. A greater degree of curvature of the segment 52 corresponds to a greater curve at the distal tip of the guidewire. Thus, it may not be necessary for the physician to monitor the distal tip of the guidewire fluoroscopically in order to evaluate the degree of curvature at the distal tip.

FIG. 4C shows, less diagrammatically, a preferred embodiment of the arrangement of sleeve 58 and clamps 59. The arrangement includes the elongate flexible polymeric sleeve 58 containing a malleable wire 62 extending therethrough. The sleeve 58 is provided with an eccentrically disposed bore 60 adapted to receive the guidewire. In the illustrative embodiment, the ends of the sleeve may be beveled as indicated at 65 so that the bore 60 for the guidewire is shorter than the bore 63 that receives the malleable wire 62. Each of the clamps, indicated generally at 59, preferably is in the form of a collet having a fixed portion 67 and a rotatable portion 68 threaded to the fixed portion 67. The fixed portion 67 includes integral bendable fingers 69 which surround and are tightened about the guidewire 10 when the rotatable collet portion 68 is tightened. The opposite end of the fixed collet portion 67 is in the form of a tubular element 71 that receives and is adhesively attached to an end of the sleeve 58. As shown in FIG. 4C, the axis of the bore 60 in the sleeve 58 is offset from that of the collet 59 so that a portion 73 of the guidewire 10 must bend slightly as it passes between the collet 68 and the sleeve 58. In order to guide the guidewire 10 between the collet 68 and sleeve 58, a guide tube 75 may be provided. The guide tube may be formed from hypodermic tubing. It is adhesively attached, at its ends to the collet 59 and sleeve 58 as shown. Thus, the sleeve 58 may be secured at its ends to the guidewire in order to cause a tension to be applied to the pull wire when the sleeve 58 is bent, as described. Alternately, the collet connector elements 59 may be released from their gripping engagement on the guidewire to permit the sleeve 58 to be removed so that the guidewire may be extended and a catheter exchange performed over the extended wire.

Should it be desired to perform a catheter exchange, the flexible segment 52 is straightened out to permit the sleeve 58 to be withdrawn off the proximal end of the guidewire. The guidewire extension 70 (FIG. 8) then may be connected t the guidewire by insertion of the connector end of the extension wire and into the tubular socket 54 as described in aforesaid U.S. Pat. Application Ser. No. 206,008, the disclosure of which is hereby incorporated by reference. The catheter exchange then may be performed and the guidewire extension 70 then may be detached. The sleeve 58 then may be slipped over the proximal end of the guidewire, onto the flexible segment 52 in readiness to reset the curvature at the distal end of the guidewire as may be desired.

From the foregoing, it will be appreciated that the invention provides a steerable guidewire in which the distal tip may be curved variably and adjustably by control from the proximal end of the guidewire and in which the guidewire also is connectable to a guidewire extension to permit catheter exchanges. The invention provides numerous advantages, some of which are that that the degree of curvature is easily adjusted by the physician's simple single handed manipulation; the degree of curvature at the proximal end of the guidewire provides an immediate indication of the degree of curvature at the distal end without the need to resort to fluoroscopic monitoring; the outer diameter of the guidewire, including its entire proximal portion remains constant thereby facilitating guidewire exchanges; a means is provided for retaining the curvature at the distal end of the guidewire in any predetermined configuration; no complex awkward mechanisms are required in order to control the pull wire; and the device is of simple construction and is easy to use. It should be understood, however, that the foregoing description of the invention is intended merely to be illustrative thereof and that other embodiments, modifications and equivalents may be apparent to those skilled in the art without departing from its spirit.

Having thus described the invention, what I desire to claim and secure by Letters Patent is:

1. A steerable guidewire comprising:
   an elongate solid walled tubular shaft having a proximal end and a distal end;
   an elongate flexible distal segment connected to and extending distally from the shaft, the distal segment being flexible;
   a pull wire extending through the tubular shaft and into the flexible distal segment, the distal end of the pull wire being connected to the distal portion of the flexible segment in a manner such that when tension is applied to the pull wire, the distal end of the flexible distal segment will assume a curved configuration;
   the shaft including a flexible stretchable tubular segment at a proximal portion distally of the proximal end of the shaft;
   the pull wire extending through the flexible stretchable tubular segment and being attached to the shaft proximally of the flexible segment.

2. A guidewire as defined in claim 1 wherein a portion of the shaft proximally of the flexible stretchable tubular segment comprises connector means for connection to an end of a guidewire extension.

3. A guidewire as defined in claim 2 wherein said connector means comprises:
   an elongate tubular socket attached to and extending proximally of the flexible stretchable segment, the socket being adapted to receive a connector element of the guidewire extension.

4. A steerable guidewire as defined in any of claims 2 or 3 wherein the flexible stretchable tubular segment is formed from an elastomeric material.

5. A steerable guidewire as defined in any of claims 2 or 3 further comprising means detachably connectible with the proximal portion of the shaft for effecting stretching of the tubular segment and causing a tension to be applied by the pull wire in response to bending of the flexible stretchable tubular segment.

6. A steerable guidewire as defined in claim 1 wherein the shaft of the guidewire includes an elongate tubular element attached to the proximal end of the flexible stretchable tubular segment and having an open proximal end thereby to define a socket to receive a guidewire extension.

7. A steerable guidewire as defined in claim 1 wherein the flexible stretchable tubular segment is formed form an elastomeric material.

8. A steerable guidewire as defined in claim 7 wherein the shaft of the guidewire includes an elongate tubular element attached to the proximal end of the flexible stretchable tubular segment and having an open proximal end thereby to define a socket to receive a guidewire extension.

9. A steerable guidewire as defined in claim 1 further comprising means detachably connectible with the proximal portion of the shaft for effecting stretching of the tubular segment and causing a tension to be applied by the pull wire in response to bending of the flexible stretchable tubular segment.

10. A guidewire as defined in claim 9 wherein the detachably connectible means comprises an elongate flexible sleeve having a longitudinal axis and a longitudinally extending bore laterally displaced from the axis, the bore being adapted to receive the guidewire and means for detachably receiving the sleeve to the guidewire at opposite ends of the flexible stretchable tubular segment.

11. A steerable guidewire as defined in claim 9 wherein the shaft of the guidewire includes an elongate tubular element attached to the proximal end of the flexible stretchable tubular segment and having an open proximal end thereby to define a socket to receive a guidewire extension.

12. A guidewire as defined in claim 10 further comprising means for retaining the sleeve in a bent configuration.

13. A steerable guidewire as defined in claim 10 wherein the shaft of the guidewire includes an elongate tubular element attached to the proximal end of the flexible stretchable tubular segment and having an open proximal end thereby to define a socket to receive a guidewire extension.

14. A guidewire as defined in claim 12 wherein the means for retaining the sleeve in the bent configuration comprises a longitudinally extending malleable element disposed within the sleeve.

15. A steerable guidewire as defined in claim 12 wherein the shaft of the guidewire includes an elongate tubular element attached to the proximal end of the flexible stretchable tubular segment and having an open proximal end thereby to define a socket to receive a guidewire extension.

16. A steerable guidewire as defined in claim 14 wherein the shaft of the guidewire includes an elongate tubular element attached to the proximal end of the flexible stretchable tubular segment and having an open proximal end thereby to define a socket to receive a guidewire extension.

17. A guidewire as defined in claim 16 wherein the proximal end of the pull wire is attached to the elongated tubular member.

18. A steerable guidewire comprising:

an elongate solid walled tubular shaft having a proximal end and a distal end;

an elongate flexible distal segment connected to and extending distally from the shaft, the distal segment being flexible;

a pull wire extending through the tubular shaft and into the flexible distal segment, the distal end of the pull wire being connected to the distal portion of the flexible segment in a manner such that when tension is applied to the pull wire, the distal end of the flexible distal segment will assume a curved configuration;

the shaft including a flexible stretchable tubular segment at a proximal portion distally of the proximal end of the shaft, the flexible stretchable tubular segment having a proximal end and a distal end;

the pull wire extending through the flexible stretchable tubular segment and being anchored with respect to the proximal end of the flexible stretchable tubular segment.

19. A guidewire as defined in claim 18 wherein the pull wire is anchored at the proximal end of the flexible stretchable tubular segment.

* * * * *